US012714505B2

(12) United States Patent
Zhao et al.

(10) Patent No.: US 12,714,505 B2
(45) Date of Patent: Aug. 25, 2026

(54) SURGICAL MARGIN PATH GENERATING METHOD AND SYSTEM FOR TUMOR SURGERY AND STORAGE MEDIUM

(71) Applicant: XIANGYA HOSPITAL CENTRAL SOUTH UNIVERSITY, Changsha (CN)

(72) Inventors: Shuang Zhao, Changsha (CN); Kai Huang, Changsha (CN); Xiang Chen, Changsha (CN); Zixi Jiang, Changsha (CN)

(73) Assignee: XIANGYA HOSPITAL CENTRAL SOUTH UNIVERSITY, Changsha (CN)

( * ) Notice: Subject to any disclaimer, the term of this patent is extended or adjusted under 35 U.S.C. 154(b) by 161 days.

(21) Appl. No.: 18/901,995

(22) Filed: Sep. 30, 2024

(65) Prior Publication Data

US 2025/0017663 A1 Jan. 16, 2025

Related U.S. Application Data

(63) Continuation of application No. PCT/CN2023/077783, filed on Feb. 23, 2023.

(30) Foreign Application Priority Data

Apr. 13, 2022 (CN) ......................... 202210389690.9

(51) Int. Cl.
*A61B 34/10* (2016.01)
*G16H 10/60* (2018.01)

(52) U.S. Cl.
CPC ............. *A61B 34/10* (2016.02); *G16H 10/60* (2018.01); *A61B 2034/107* (2016.02)

(58) Field of Classification Search
CPC .............. A61B 34/10; A61B 2034/107; A61B 2034/105; G16H 10/60; G16H 30/40;
(Continued)

(56) References Cited

U.S. PATENT DOCUMENTS

2018/0294052 A1* 10/2018 Fishman ............ G06Q 10/1093
2019/0365475 A1* 12/2019 Krishnaswamy ...... A61B 90/17
(Continued)

FOREIGN PATENT DOCUMENTS

CN 111067473 A 4/2020
CN 113785328 A 12/2021
CN 114298980 A 4/2022

*Primary Examiner* — Jennifer Mehmood
*Assistant Examiner* — Vaisali Rao Koppolu
(74) *Attorney, Agent, or Firm* — George D. Morgan

(57) ABSTRACT

The present invention relates to the technical field of computer-aided preoperative analysis, and discloses a surgical margin path generating method and system for tumor surgery and a storage medium. The method comprises: acquiring clinical pictures of a tumor, dermatoscopy pictures, and medical history information of patients; segmenting and extracting tumor boundaries from the dermatoscopy pictures by using a preset deep learning network model to obtain skin tumor boundaries under a dermoscope; registering the skin tumor boundaries with the clinical pictures to obtain target tumor boundaries; generating an initial surgical margin path according to the medical history information, the target tumor boundaries, and a preset path generating model; in the case of a benign tumor, smoothing the initial surgical margin path to generate a surgical margin path of a fusiform incision.

6 Claims, 3 Drawing Sheets

(58) Field of Classification Search

CPC ...... G16H 50/20; G16H 30/20; G06T 7/0012; G06T 7/12; G06T 7/13; G06T 7/30; G06T 2207/20081; G06T 2207/20084; G06T 2207/30096; G06N 3/045; G06N 3/08

See application file for complete search history.

(56) References Cited

U.S. PATENT DOCUMENTS

2020/0126235 A1* 4/2020 Witte ........................ G06T 7/11
2022/0211273 A1* 7/2022 Lu .......................... A61B 5/444
2025/0029255 A1* 1/2025 Wang ........................ G06T 7/13
2025/0032188 A1* 1/2025 Jang ....................... A61B 34/10

* cited by examiner

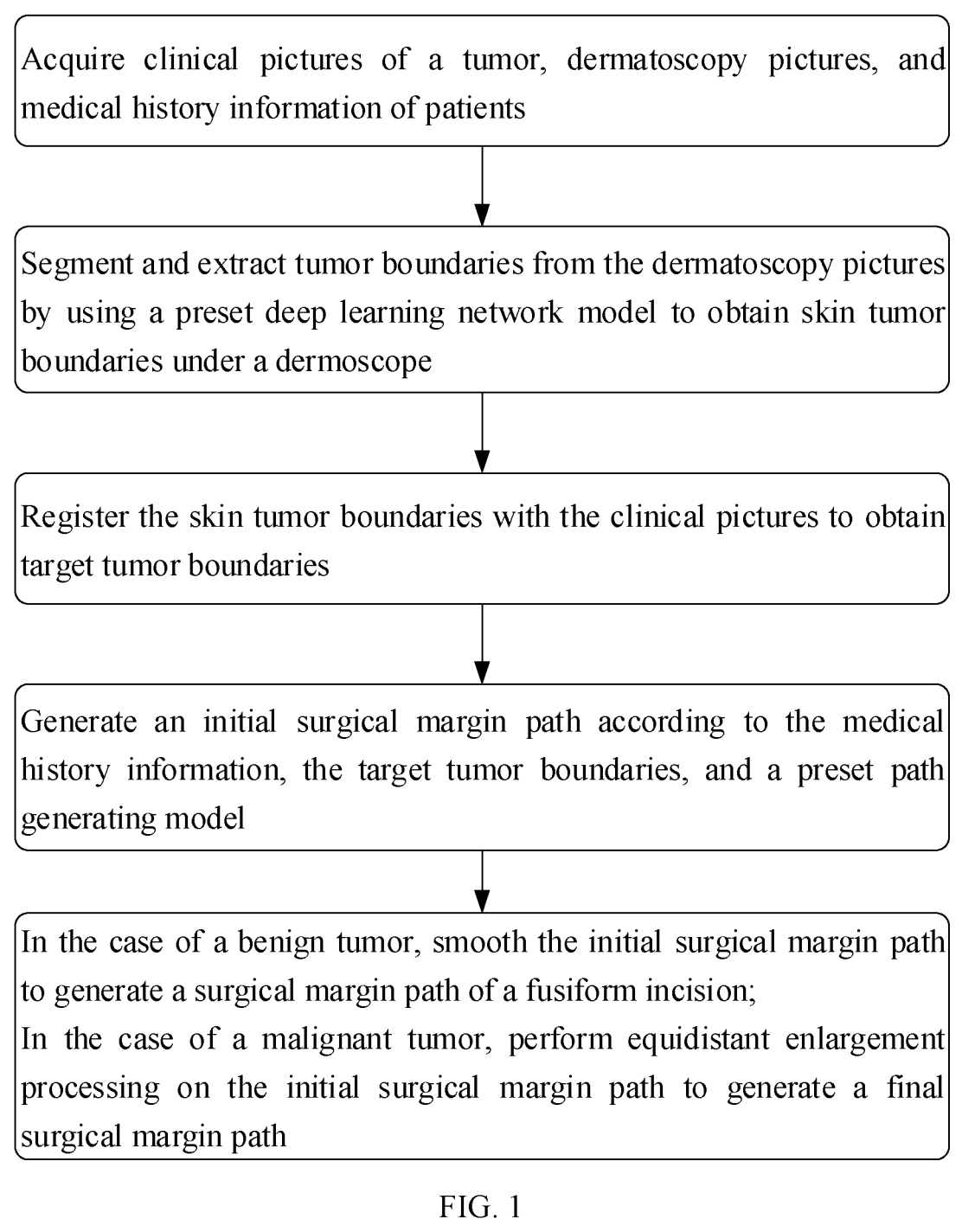

Acquire clinical pictures of a tumor, dermatoscopy pictures, and medical history information of patients Segment and extract tumor boundaries from the dermatoscopy pictures by using a preset deep learning network model to obtain skin tumor boundaries under a dermoscope Register the skin tumor boundaries with the clinical pictures to obtain target tumor boundaries Generate an initial surgical margin path according to the medical history information, the target tumor boundaries, and a preset path generating model In the case of a benign tumor, smooth the initial surgical margin path to generate a surgical margin path of a fusiform incision;
In the case of a malignant tumor, perform equidistant enlargement processing on the initial surgical margin path to generate a final surgical margin path

FIG. 1

SURGICAL MARGIN PATH GENERATING METHOD AND SYSTEM FOR TUMOR SURGERY AND STORAGE MEDIUM

CROSS-REFERENCE TO RELATED APPLICATIONS

The application claims priority to Chinese patent application No. 2022103896909, filed on Apr. 13, 2022, the entire contents of which are incorporated herein by reference.

TECHNICAL FIELD

The present invention relates to the technical field of computer-aided preoperative analysis, and in particular to a surgical margin path generating method and system for tumor surgery and a storage medium.

BACKGROUND

Currently, in clinical practice, design of surgical margins of skin tumors is mainly marked according to doctor's own experience. Design by doctors according to own experience mainly relies on their subjective judgment, thereby resulting in poor objectivity; and moreover, design of a fusiform is not strictly quantified and is manually drawn by doctors, such that the accuracy of the shape and area of an incision is difficult to guarantee by manually drawing the fusiform. Thus, the surgical margin designed by this method is prone to generating problems such as too large or too small excision area, and inaccurate surgical margin design.

Herein, when the excision area is too large, a wound becomes larger, healing time is prolonged, and remaining skin in the area is stretched after healing, which affects normal function and results in poor aesthetics. The skin at the surgical margin is difficult in apposition when being sutured, which can easily lead to scar formation. In the later stage, scar contraction can damage skin function and affect aesthetics. After deep tissues are sutured, it is easy to generate gaps due to insufficient apposition, which not only makes it difficult for a surgical site to heal, but also increases the risk of anaerobic bacterial infection, making it difficult to achieve primary healing. If the excision area is too small, it is difficult to completely excise tumors, and residual tumor cells will continue to proliferate, leading to recurrence. It can be seen that there is an urgent need to provide a surgical margin path generating method for tumor surgery.

SUMMARY

The present invention provides a surgical margin path generating method and system for tumor surgery and a storage medium, so as to solve the problem existing in the prior art.

In order to achieve the above objectives, the present invention is implemented through the following technical solution:

- in the first aspect, the present invention provides a surgical margin path generating method for tumor surgery, including:
- acquiring clinical pictures of a tumor, dermatoscopy pictures, and medical history information of patients;
- segmenting and extracting tumor boundaries from the dermatoscopy pictures by using a preset deep learning network model to obtain skin tumor boundaries under a dermoscope;

- registering the skin tumor boundaries with the clinical pictures to obtain target tumor boundaries;
- generating an initial surgical margin path according to the medical history information, the target tumor boundaries, and a preset path generating model;
- in the case of a benign tumor, smoothing the initial surgical margin path to generate a surgical margin path of a fusiform incision; and
- in the case of a malignant tumor, performing equidistant enlargement processing on the initial surgical margin path to generate a final surgical margin path.

Optionally, the medical history information of the patient includes personal basic information, current medical history, past medical history, personal history, and physical examination information.

Optionally, before the medical history information and the target tumor boundaries are inputted into the preset path generating model, the method further includes:

- collecting N historical clinical pictures of the tumor, N dermatoscopy pictures, medical history information of a patient with the tumor, and a corresponding surgical margin path of the tumor;
- determining the type of the tumor according to the medical history information of the patient with the tumor; and
- by using the N historical clinical pictures, the N dermatoscopy pictures, and the type of the tumor as inputs, and the surgical margin path corresponding to the tumor as an output of the network model, performing iterative training to obtain the preset path generating model.

Optionally, generating an initial surgical margin path according to the medical history information, the target tumor boundaries, and a preset path generating model includes: determining the type of the tumor according to the medical history information;

- in the case of a benign tumor, generating the initial surgical margin path on the basis of enlarging the target tumor boundaries by 1 mm-5 mm; and
- in the case of a malignant tumor, generating the initial surgical margin path on the basis of enlarging the target tumor boundaries by 5 mm-20 mm.

Optionally, in the case of a benign tumor, smoothing the initial surgical margin path to generate a surgical margin path of a fusiform incision includes:

- determining skin dermal ridges around a skin lesion of the tumor; and
- designing the surgical margin path of the fusiform incision in a direction parallel to the skin dermal ridges according to a preset manner, where the surgical margin path of the fusiform incision includes a first end angle, a second end angle, width of a fusiform, and a long axis of the fusiform.

The preset manner includes:

- setting both the first end angle and the second end angle of a fusiform as 30 degrees;
- designing the width of the fusiform in the direction being perpendicular to the skin dermal ridges, where the width of the fusiform is obtained by extending two ends of a tumor in the direction of length, being perpendicular to that of the skin dermal ridges by 2 mm;
- designing the long axis of the fusiform in the direction being parallel to the skin dermal ridges to be 2-3 times the width of the fusiform.

Optionally, the method further includes:

- projecting the surgical margin path of the fusiform incision corresponding to the benign tumor or the final surgical margin path corresponding to the malignant tumor onto the skin surface of the patient.

In the second aspect, the present application provides a surgical margin path generating system for tumor surgery, including a memory, a processor, and a computer program stored on the memory and executable on the processor, where the processor implements the steps of the method of the first aspect when executing the computer program.

In the third aspect, the present application provides a computer-readable storage medium storing a computer program thereto, where when executed by a processor, the program implements the steps of the method of the first aspect.

Beneficial Effects according to the surgical margin path generating method for tumor surgery, provided by the present invention, firstly, the initial surgical margin path is generated according to the medical history information, the target tumor boundaries, and the preset path generating model; in the case of the benign tumor, the initial surgical margin path is smoothed to generate the surgical margin path of the fusiform incision; and in the case of the malignant tumor, equidistant enlargement processing is performed on the initial surgical margin path to generate the final surgical margin path. In this way, the dermatoscopy pictures are taken as a factor to consider, and skin information can be discovered more accurately. By using the preset path generating model, a more accurate surgical margin path can be automatically generated, and different final surgical margin paths can be determined for different types of tumors, which can avoid errors caused by artificial design from causing a too large excision area to affect healing, increase infection risks, and cause more serious skin problems, or from causing a too small excision area to cause recurrence. Replacing manually designing surgical margins by doctors with this method can significantly shorten preoperative preparation time, and have higher efficiency while improving accuracy.

BRIEF DESCRIPTION OF THE DRAWINGS

FIG. 1 is a flowchart of a surgical margin path generating method for tumor surgery according to a preferred embodiment of the present invention;

DETAILED DESCRIPTION OF THE EMBODIMENTS

Figure 2:
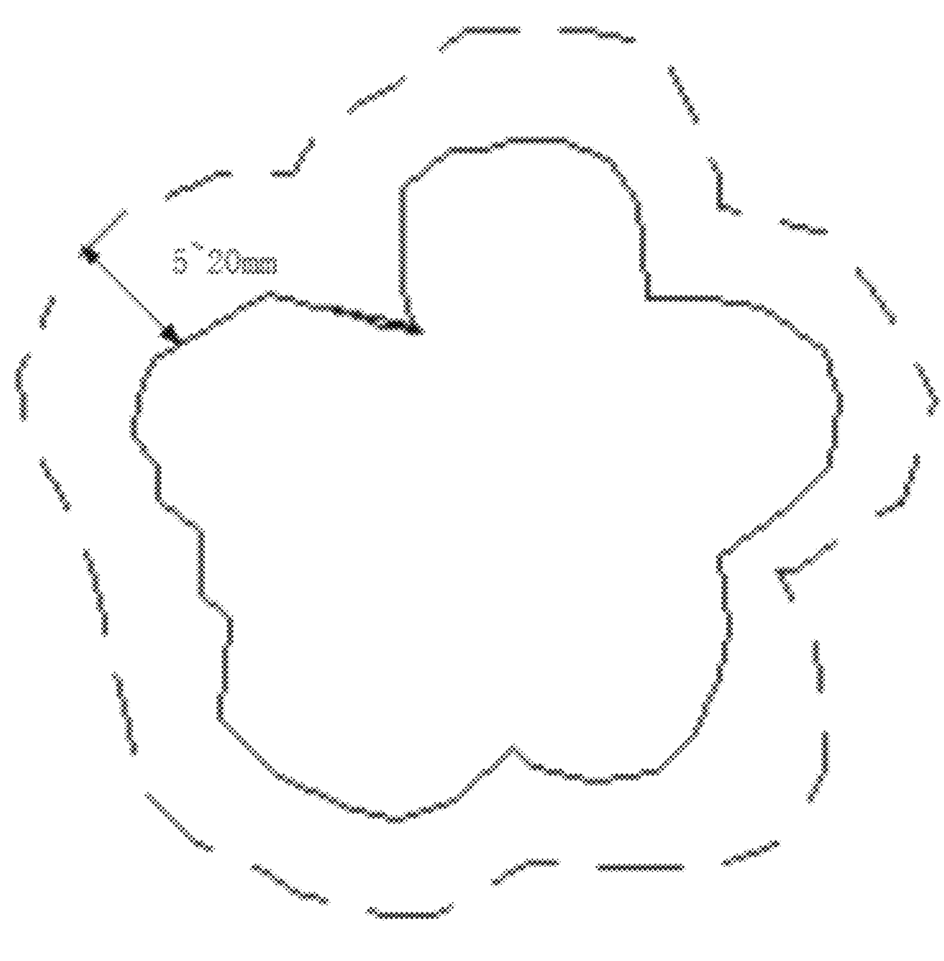
FIG. 2 is a schematic diagram of an equidistant enlarged surgical margin path designed for a malignant tumor according to a preferred embodiment of the present invention.

The technical solution of the present invention will be clearly and completely described in the following with reference to the accompanying drawings. It is obvious that the embodiments to be described are only a part rather than all of the embodiments of the present invention. All other embodiments obtained by a person of ordinary skill in the art based on the embodiments of the present invention without creative efforts shall fall within the protection scope of the present invention.

Unless otherwise defined, the technical or scientific terms used in the present invention shall have the common meanings as understood by those skilled in the art to which the present invention belongs. The terms "first", "second", and the like, used in the present invention are not intended to indicate any sequence, amount or importance, but distinguish different components. Also, the terms such as "a", "an", and the like are not intended to limit the amount, but indicate the existence of at least one. As used herein, "connection", "connected", and the like are not limited to a physical or mechanical connection but may include a direct or indirect electrical connection. "Upper", "lower", "left", "right", and the like are only used to indicate relative position relationship, and when the absolute position of the described object changes, the relative position relationship may be changed accordingly.

Referring to FIG. 1, the embodiments of the present application provide a surgical margin path generating method for tumor surgery, including:

- acquiring clinical pictures of a tumor, dermatoscopy pictures, and medical history information of patients;
- segmenting and extracting tumor boundaries from the dermatoscopy pictures by using a preset deep learning network model to obtain skin tumor boundaries under a dermoscope;
- registering the skin tumor boundaries with the clinical pictures to obtain target tumor boundaries;
- generating an initial surgical margin path according to the medical history information, the target tumor boundaries, and a preset path generating model;
- in the case of a benign tumor, smoothing the initial surgical margin path to generate a surgical margin path of a fusiform incision; and
- in the case of a malignant tumor, performing equidistant enlargement processing on the initial surgical margin path to generate a final surgical margin path.

In the embodiments, the clinical pictures can be obtained through a tablet computer or related image acquisition equipment, and the dermatoscopy pictures can be obtained under the dermoscope. Herein, the dermoscope can magnify skin features that are difficult for naked eyes to recognize, such that the dermatoscopy pictures obtained by using the dermoscope can accurately capture actual information of the skin. By using the dermatoscopy pictures for analysis, the actual skin condition of the patient can be more accurately obtained. The actual skin condition is used as input data to avoid situations where body surface boundaries do not comply with an actual lesion range.

Specifically, in the case of the malignant tumor, as shown in FIG. 2, when equidistant enlargement processing is performed on the initial surgical margin path to generate the final surgical margin path, a specific multiple of equidistant enlargement can be set according to a specific grade of the malignant tumor. In this way, different surgical margin ranges can be set for different types of malignant tumors, which can effectively prevent recurrence.

According to the surgical margin path generating method for tumor surgery, firstly, the initial surgical margin path is generated according to the medical history information, the target tumor boundaries, and the preset path generating model; in the case of the benign tumor, the initial surgical margin path is smoothed to generate the surgical margin path of the fusiform incision; and in the case of the malignant tumor, equidistant enlargement processing is performed on the initial surgical margin path to generate the final surgical margin path. In this way, the dermatoscopy pictures are taken as a factor to consider, and skin information can be discovered more accurately. By using the preset path generating model, a more accurate surgical margin generating path can be automatically generated, and different final surgical margin paths can be determined for different types of tumors, which can avoid errors caused by artificial design from causing a too large excision area to affect healing, increase infection risks, and cause more serious skin problems, or from causing a too small excision area to cause recurrence. Replacing manually designing surgical margins by doctors with this method can significantly shorten preoperative preparation time, and have higher efficiency while improving accuracy.

Optionally, the medical history information of the patient includes personal basic information, current medical history, past medical history, personal history, and physical examination information.

In the optional embodiments, the personal basic information includes the name, age, place of origin, and other information of the patient; the current medical history includes a time log of illness for the patient, the name of the illness, and examination results; the past medical history includes the past illness situation of the patient; the personal history includes social experience, occupation and working conditions of the patient, habits and hobbies, travel history, drug use history, and the like of the patient; and the physical examination information includes the height, weight, and other physical information of the patient, which is only an example but not a limitation.

Optionally, before the medical history information and the target tumor boundaries are inputted into the preset path generating model, the method further includes:

collecting N historical clinical pictures of the tumor, N dermatoscopy pictures, medical history information of the patient with the tumor, and a corresponding surgical margin path of the tumor;

determining the type of the tumor according to the medical history information of the patient with the tumor; and by using the N historical clinical pictures, the N dermatoscopy pictures, and the type of the tumor as inputs, and the surgical margin path corresponding to the tumor as an output of the network model, performing iterative training to obtain the preset path generating model.

When the preset path generating model is trained, information of the patient can be randomly divided into a training set and a validation set in a proportion of 7:3. Data in the training set is used for constructing a model, and data in the training set is used for testing and adjusting the model in the next step. A surgical margin design algorithm is constructed on the basis of a convolutional neural network, which can be used for recognizing tumor margins according to the inputted clinical pictures and the inputted dermatoscopy pictures.

Optionally, generating an initial surgical margin path according to the medical history information, the target tumor boundaries, and a preset path generating model, includes:

determining the type of the tumor according to the medical history information, in the case of the benign tumor, generating the initial surgical margin path on the basis of enlarging the target tumor boundaries by 1 mm-5 mm; and in the case of the malignant tumor, generating the initial surgical margin path on the basis of enlarging the target tumor boundaries by 5 mm-20 mm.

where determining the type of the tumor according to the medical history information can be realized by determining the growth condition of the tumor according to the medical history information so as to further determine the type of the tumor. In one embodiment, the type of the tumor can also be determined by combining the medical history information with the current thickness of the tumor.

Figure 3:
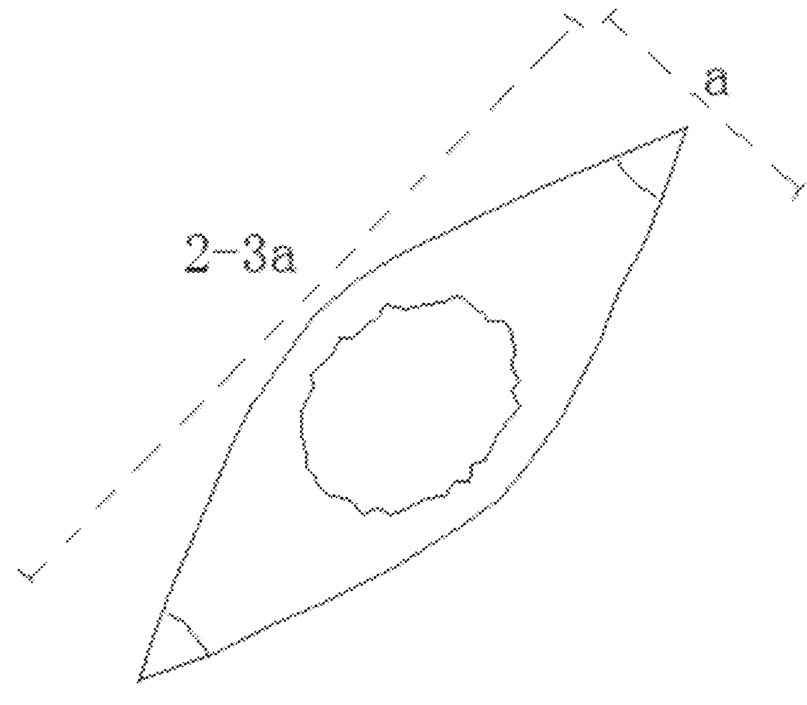
FIG. 3 is a schematic diagram of a fusiform surgical margin path designed for a benign tumor according to a preferred embodiment of the present invention.

Referring to FIG. 3, in the case of a benign tumor, smoothing the initial surgical margin path to generate a surgical margin path of a fusiform incision, includes: determining skin dermal ridges around a skin lesion of the tumor; and designing the surgical margin path of the fusiform incision in a direction parallel to the skin dermal ridges according to a preset manner, where the surgical margin path of the fusiform incision includes a first end angle, a second end angle, width of a fusiform, and a long axis of the fusiform.

The preset manner includes:

setting both the first end angle and the second end angle of a fusiform as 30 degrees;

designing the width of the fusiform in the direction being perpendicular to the skin dermal ridges, where the width of the fusiform is obtained by extending two ends of a tumor in the direction of length, being perpendicular to that of the skin dermal ridges by 2 mm; and designing a long axis of the fusiform in the direction being parallel to the skin dermal ridges to be 2-3 times the width of the fusiform.

It should be noted that the width of the fusiform perpendicular to the direction of the skin dermal ridges is set as a, and the length of the long axis can be adjusted within a range of 2-3a according to the aesthetic expectations, tumor location, and the degree of malignancy of the tumor of the patient.

Optionally, the method further includes:

projecting the surgical margin path of the fusiform incision corresponding to the benign tumor or the final surgical margin path corresponding to the malignant tumor onto the skin surface of the patient. In this way, it can facilitate doctors to directly perform relevant operations on the basis of projection, thereby reducing influence of human factors, and achieving more accurate excision.

Optionally, the accuracy of the model for surgical margin design, that is, a coincidence rate between the surgical margin designed by through model and the surgical margin manually depicted by the doctor, can be tested in the training set on the basis of using the clinical pictures completed for surgical margin design and depiction as a standard, and the model can be gradually corrected and optimized on the basis of the above results. In this way, through correction and optimization, the obtained results can be more accurate.

The embodiments of the present application further provide a surgical margin path generating system for tumor surgery, including a memory, a processor, and a computer program stored on the memory and executable on the processor, where the processor implements the steps of the method when executing the computer program.

The surgical margin path generating system for tumor surgery can implement the embodiments of the surgical margin path generating method for tumor surgery, and can achieve the same beneficial effects, and thus, it will not be repeated here.

The embodiments of the present application further provides a computer-readable storage medium storing a computer program thereto, which implements the steps of the method when executing the program.

The computer-readable storage medium can implement the embodiments of the surgical margin path generating method for tumor surgery, and can achieve the same beneficial effects, and thus, it will not be repeated here.

The above provides a detailed description of the preferred embodiments of the present invention. It should be understood that those skilled in the art can make many modifications and changes according to the concept of the present invention without creative labor. Thus, any technical solution that can be obtained by those skilled in the art on the basis of the concept of the present invention through logical analysis, logical inference, or limited experiments on the basis of the prior art should fall into the scope of protection determined by the claims.

What is claimed is:

1. A surgical margin path generating method for tumor surgery, comprising:

acquiring clinical pictures of a tumor, dermatoscopy pictures, and medical history information of patients;

segmenting and extracting tumor boundaries from the dermatoscopy pictures by using a preset deep learning network model to obtain skin tumor boundaries under a dermoscope;

registering the skin tumor boundaries with the clinical pictures to obtain target tumor boundaries;

generating an initial surgical margin path according to the medical history information, the target tumor boundaries, and a preset path generating model;

in the case of a benign tumor, smoothing the initial surgical margin path to generate a surgical margin path of a fusiform incision; and in the case of a malignant tumor, performing equidistant enlargement processing on the initial surgical margin path to generate a final surgical margin path;

before the medical history information and the target tumor boundaries are inputted into the preset path generating model, the method further comprises:

collecting at least one historical clinical pictures of the tumor, at least one dermatoscopy pictures, medical history information of a patient with the tumor, and a corresponding surgical margin path of the tumor;

determining the type of the tumor according to the medical history information of the patient with the tumor; and by using the at least one historical clinical pictures, the at least one dermatoscopy pictures, and the type of the tumor as inputs, and the surgical margin path corresponding to the tumor as an output of the network model, performing iterative training to obtain the preset path generating model;

generating an initial surgical margin path according to the medical history information, the target tumor boundaries, and a preset path generating model comprises:

determining the type of the tumor according to the medical history information;

in the case of a benign tumor, generating the initial surgical margin path on the basis of enlarging the target tumor boundaries by 1 mm-5 mm; and in the case of a malignant tumor, generating the initial surgical margin path on the basis of enlarging the target tumor boundaries by 5 mm-20 mm.

2. The surgical margin path generating method for tumor surgery according to claim 1, wherein the medical history information of the patient comprises personal basic information, current medical history, past medical history, personal history, and physical examination information.

3. The surgical margin path generating method for tumor surgery according to claim 1, wherein in the case of a benign tumor, smoothing the initial surgical margin path to generate a surgical margin path of a fusiform incision comprises:

determining skin dermal ridges around a skin lesion of the tumor;

designing the surgical margin path of the fusiform incision in a direction parallel to the skin dermal ridges according to a preset manner, wherein the surgical margin path of the fusiform incision comprises a first end angle, a second end angle, width of a fusiform, and a long axis of the fusiform;

the preset manner comprises:

setting both the first end angle and the second end angle of a fusiform as 30 degrees;

designing the width of the fusiform in the direction being perpendicular to the skin dermal ridges, wherein the width of the fusiform is obtained by extending two ends of a tumor in the direction of length, being perpendicular to that of the skin dermal ridges by 2 mm; and designing the long axis of the fusiform in the direction being parallel to the skin dermal ridges to be 2-3 times the width of the fusiform.

4. The surgical margin path generating method for tumor surgery according to claim 1, further comprising:

projecting the surgical margin path of the fusiform incision corresponding to the benign tumor or the final surgical margin path corresponding to the malignant tumor onto the skin surface of the patient.

5. A surgical margin path generating system for tumor surgery, comprising a memory, a processor, and a computer program stored on the memory and executable on the processor, wherein the processor implements the steps of the method of claim 1 when executing the computer program.

6. A non-transitory computer-readable storage medium storing a computer program, wherein when executed by a processor, the program implements the steps of the method of claim 1.

* * * * *